United States Patent [19]

Horwath

[11] Patent Number: 4,490,466

[45] Date of Patent: Dec. 25, 1984

[54] METHOD FOR SCREENING MICROORGANISMS FOR THE PRODUCTION OF AMYLOLYTIC ENZYMES

[75] Inventor: Robert O. Horwath, Westport, Conn.

[73] Assignee: Nabisco Brands, Inc., Parsippany, N.J.

[21] Appl. No.: 480,430

[22] Filed: Mar. 30, 1983

[51] Int. Cl.$^3$ .......................... C12Q 1/40; C12Q 1/04
[52] U.S. Cl. ...................................... 435/22; 435/34; 435/801
[58] Field of Search .................. 435/22, 34, 201, 202, 435/203, 801

[56] References Cited

FOREIGN PATENT DOCUMENTS 1296839 11/1972 United Kingdom ............... 435/202

*Primary Examiner*—Lionel M. Shapiro
*Attorney, Agent, or Firm*—Richard Kornutik

[57] ABSTRACT

Described is a process for screening of microorganisms for the production of amylolytic enzymes. Microorganisms capable of amylolytic enzyme synthesis and growing on the surface of a solid medium are detected by identifying a zone of hydrolyzed starch surrounding each microorganism. The process is particularly useful for the detection of α-amylase activity in strains of *Bacillus licheniformis* as it employs a selection step under anaerobic conditions prior to the detection of the enzyme.

7 Claims, No Drawings

METHOD FOR SCREENING MICROORGANISMS FOR THE PRODUCTION OF AMYLOLYTIC ENZYMES

FIELD OF THE INVENTION

This invention relates to the field of microbiology and more particularly to the selection and screening of microorganisms.

BACKGROUND OF THE INVENTION

A variety of approaches has been used to improve the economy of biologically-based industrial processes by "improving" the organism involved. These techniques constitute what may be categorized as strain improvement programs. The efficacy of improving said processes is dependent on the type of organism and the nature of the end-product.

The success of any strain improvement program will be directly affected by the facility with which genetic diversity can be generated in the subject organism, or alternatively the ease with which the genetic diversity already present in nature can be evaluated.

A colony that appears on agar medium following plating out of spores, cells, or small hyphal fragments consists of a population most of which are genetically identical, although some cells may differ due to spontaneous mutation during the growth of the colony or to nuclear heterogeneity in the original propagule.

It was the rare occurrence of spontaneous mutations within existing cultures that provided the major source of strain improvement germplasm in the early years of the fermentation industry. A secondary source of improved strains was nature itself, that is, the isolation from nature of previously unknown strains with improved characteristics.

As a fuller understanding of the biological and chemical basis of genetic change developed, strain improvement programs incorporated this new knowledge into their rationale. For example, induced mutagenesis to generate genetic diversity followed by the subsequent screening, selection and purification of superior strains represents one of the most effective means of improving the yield of a fermentation product. Mutation programs are vital to the fermentation industry in that higher productivities exhibited by the new strains are essential in reducing costs.

It is now appreciated that the choice of a particular mutagen as well as the actual conditions of mutagenesis can play a major role in determining the types and numbers of mutants recovered during a strain improvement program. In general, two experimental approaches have been used to recover new strains resulting from induced mutagenesis experiments; these are: screening and selection.

In a screening system all strains grow with the exception of those killed outright as a result of the mutagenesis treatment; thus each isolate must be examined to identify the desired characteristic. Since tens of millions of isolates must be examined, this approach can be highly labor intensive.

In a selection system, the experimental conditions are chosen so as to establish a growth differential between the rare strains possessing the desired characteristic and all other strains which do not possess said trait. In certain instances the selected strain will not grow under the conditions of the experiment while the non-selected strains will grow. Thus, by removing the growing strains by filtration or other means, the size of the population of cells remaining to be examined is dramatically reduced. Alternatively, conditions may be established such that the selected strain will grow while the non-selected strains are inhibited, here again effectively reducing the population to be examined.

Although induced mutagenesis has been an extremely powerful force in the area of strain improvement, there are some limitations. For example, as more and more mutations are accumulated in a strain as a result of the continuing improvement program, a saturation level is reached. Subjecting such a strain to further selection often results in a loss of productivity due to reversion of existing mutations.

A more fundamental limtation exists in induced-mutation based improvement programs, namely, such programs are based on the assumption that the strains possess the activity to be improved. In other words, the organism must possess, in its genetic repertoire, the information to direct the synthesis of a gene product before any genetically-based improvement program relating to the function of the product may be considered.

A variety of genetic approaches has been developed to reduce these limitations. For example, hybridization techniques allow for genetic recombination to occur among a number of different strains. Hybridization can be achieved by means of sexual reproduction or asexual processes such as somatic cell fusion or heterokaryon formation. The advent of recombinant DNA technology has reduced the limitations on improvement programs even further. The ability to transfer genes between organisms of widely divergent genetic backgrounds has provided the experimenter with a virtually limitless supply of genetic information upon which to improve. This advent of genetic engineering technology has prompted a renewed interest, natural sources of genetic variability, not with a view toward isolating and developing new strains, per se, but rather as a source of as little as a single gene which may be transferred to already established strains.

Regardless of the source of the variant strain, be it either nature, a spontaneous mutation, an induced mutation, or a recombinant resulting from sexual, asexual or genetic engineering processes, methods of screening and selection remain of critical importance, allowing the experimenter to recover the variant strain from among the population of existing strains from which it arose.

In light of the subject invention, one group of organisms of particular interest with regard to strain improvement programs are those useful as sources of amylolytic (starch degrading) enzymes. These enzymes fall into two main classes based upon the linkages characteristic of the substrates upon which the enzymes act. One class, the $\alpha$-1,4-glucanases contain enzymes which degrade glucose polymers having $\alpha$-1,4-linkages and do so by either randomly cleavaging at points within the polymer chain, that is they are endo-$\alpha$-1,4-glucanases or degrade the polymer from the terminus, those being characterized as exo-$\alpha$-1,4-glucanases. The endo-$\alpha$-1,4-glucanase type includes enzymes such as $\alpha$-amylase, where as the exo-$\alpha$-1,$\alpha$4-glucanase type include enzymes such as exo-maltohexohydrolase, $\beta$-amylase and amyloglucosidase.

The second class of starch degrading enzymes are the $\alpha$-1,6-glucanases, the so-called "debranching enzymes"

owing to their affinity for degrading at linkages characterizing the branch points of starch molecules. Both endo (pullulanase and isoamylase) and exo-(exo-pullulanase) forms are known.

Bacterial α-amylase (α,-1,4-glucan-glucanohydrolase, E.C. 3.2.1.1) acts, as an endolase, on starch components which contain a minimum of three linked glucose units, resulting in the formation of reducing sugars. These enzymes are useful in desizing textile fabrics, in modifying starches suitable for preparation of adhesives, sizes and coatings for the paper industry, as well as in the manufacturing of glucose, and glucose syrups. Fungal α-amylases are extensively used in flour treatment processes.

Amylases have been prepared from microbiological cultures of Bacillus. In British Specification No. 1,296,839, there is described a process for producing thermally stable alpha amylase by the cultivation of *Bacillus licheniformis*. The enzyme so produced is of significantly higher thermal stability than the α-amylase produced by *Bacillus subtilis*. However yields and activity of the enzymes recovered leave much to be desired as far as commercial production is concerned.

The disclosure by Horwath, (copending and cofiled U.S. application Ser. No. 480,428) which is incorporated herein by reference, of a new strain of *Bacillus licheniformis* particularly useful for commercial production has warranted the development of a large scale, efficient, combination selection and screening system for the recovery of α-amylase producing strains of microorganisms. It is the principle object of the instant invention to provide such a combination selection and screening system.

BRIEF DESCRIPTION OF THE INVENTION

This invention relates to a rapid, efficient combination selection and screening system for the detection of increased or decreased production of amylolytic enzymes by microorganisms.

The invention process for selecting and screening for the production of amylolytic enzymes comprises, forming a screening plate upon which is inoculated a sample of the microorganisms to be screened, incubating said microorganisms under anaerobic conditions for a sufficient period of time to permit the growth of a screenable sub-population of microorganisms, and then identifying in situ those colonies expressing amylolytic enzymes such as α-amylase, by detecting a zone of hydrolyzed starch surrounding each colony.

The detection of the hydrolyzed starch may be accomplished by merely visually identifying those colonies surrounded by a clear zone on the opaque starch containing plates. Alternatively, a starch indicating reagent may be employed to more clearly define the hydrolysis zones.

In a further embodiment, α-amylase, displaying a low calcium requirement may be distinguished from those requiring a higher level of calcium by including in the medium, a calcium chelating agent.

DETAILED DESCRIPTION OF THE INVENTION

One criterion of strain improvement is a change in the activity and/or amount of a particular enzyme produced by an organism. In general a screening procedure is employed whereby each candidate is tested for the desired change in the activity and/or amount of the enzyme. However, when evaluating a large population of potential candidates, as would be the case when attempting to isolate a new strain from nature, a screening system alone may be highly labor intensive and expensive.

In such situations it would be highly desirable to reduce the initial population of candidates by selecting therefrom a sub-population whose members would most likely display the desired trait upon subsequent screening.

As has been noted above, particularly useful microorganisms for the production of heat-stable α-amylase are members of the species *Bacillus licheniformis*. It is a preferred embodiment of the instant invention, therefore, to provide a means whereby members of the species *Bacillus licheniformis* are present among a sub-population of organisms to be screened for the presence of α-amylase activity, the sub-population having been selected from a larger population of organisms based upon a property other than the ability to produce α-amylase.

A particular valuable finding, in light of the subject invention, has been the demonstration that members of the species *Bacillus licheniformis* are facultative anaerobes. This ability to grow in the absence of oxygen distinguishes from most other amylase producing Bacilli, such as *Bacillus subtilis*, and provides the bases of a quite stringent selection system.

Thus, according to one embodiment, a soil sample is inoculated onto a solid medium which promotes the growth of a microorganism and the synthesis of α-amylase thereby. The plates are incubated under anaerobic conditions thus eliminating any strict aerobic organisms. The surviving organisms will be of two classes: strict anaerobes, those which will grow only under anaerobic conditions and facultative anaerobes those which will grow under both aerobic and anaerobic conditions. The latter class may easily be recovered by merely replating and culturing under aerobic conditions, thereby eliminating the strict anaerobes which may have appeared during the selection procedure. The surviving organisms are then screened for the presence of α-amylase by observing clearing zones around amylase producing colonies, or by reacting the medium surrounding each growing organism in situ, with an analytically indicatable reagent. A particularly useful reagent in this regard is the well-known starch iodine test. In this embodiment a clearing indicating the absence of a starch-iodine reaction in an area surrounding a colony is taken as evidence of the production of α-amylase. Since the enzyme secreted in the surrounding medium will tend to diffuse in all directions from the colony a clear halo will surround each α-amylase producing colony. The test is semi-quantitative in that a colony producing more enzyme tends to display a larger zone of clearing. Alternatively the area of hydrolyzed starch surrounding each colony may be detected by merely visually identifying a clearer zone surrounding each colony on the opaque starch-containing screening plates, particularly where thin layers of solid medium are employed.

According to a further embodiment calcium chelating agents such as nitrilo triacetic acid (NTA) or ethylene diamine tetraacetic acid (EDTA) may be added prior to the assay for α-amylase. This supplement further restricts the screenable α-amylases to those which possess a low calcium requirement for activity.

The invention as described herein provides a highly efficient selection and screening system for α-amylase producing microorganisms. A powerful selection system based upon anaerobic growth is then coupled with a screening system restricted to indicate the presence of α-amylase displaying a low calcium requirement. Although other species of microorganisms may be recovered in addition to members of the *Bacillus licheniformis* taxon, because of their selectable and screenable properties, they would also be valuable candidates for further evaluation.

To further illustrate the present invention, the following exemplification is provided.

EXAMPLE 1

This example illustrates the screening of soil samples for α-amylase producing microorganisms.

A soil sample is inoculated onto a large screening plate (1.5 liters of medium/plate) and incubated for 24–72 hours at 40° C. under anaerobic conditions.

| The aqueous medium is prepared as follows: All percentages are (w/v). | |
|---|---|
| 0.5% | Lintner Starch (Gelatinized) |
| 0.5% | Yeast Extract |
| 0.2% | Na Citrate |
| 0.5% | $(NH_4)_2HPO_4$* |
| 0.05% | $MgSO_4 \cdot 7H_2O$* |
| 0.008% | $CaCl_2 \cdot 2H_2O$* |
| | pH 7.0 |
| 1.5% | Agar |

*solutions added after autoclaving
Plates are allowed to dry 24 hours at 40° C.

After incubation, the plates are sprayed with iodine solution. The iodine solution is prepared as follows:

STOCK IODINE SOLUTION 5.50 g of C.P. (meets ACS specifications) iodine crystals are dissolved in 11.0 g KI in $H_2O$ and diluted to 250 ml.

DILUTE IODINE SOLUTION

To prepare the reagent employed as a spray, 20.0 g of KI in $H_2O$, and 2.0 ml of the stock solution above are diluted to 500 ml with $H_2O$.

Clear zones surrounding a colony are indicative of α-amylase production.

EDTA can be added to the nutrient medium used for the screening plate at a level of about 2 moles for each mole of Ca present and the screening results are then positive for only *B. licheniformis*-type strains which produce α-amylase (including for example *B. licheniformis* and *B. stearothermophilis* strains.

The Calcium-chelating agent, EDTA, suppresses α-amylase activity by any other microorganisms in which the Ca ion requirement is substantially greater than that in the *B. licheniformis* enzyme.

*B. licheniformis* and *B. stearothermophilis* strains can be distinguished by culturing at or about 60° C. where *B. licheniformis* does not grow.

What is claimed is:

1. A process for selecting and screening microorganisms for the production of amylolytic enzymes which comprises the steps of:
   (a) forming a screening plate comprising a suspension of said microorganisms on a solid medium which promotes the growth of said microroganisms and the synthesis of amylolytic enzymes thereby;
   (b) incubating said inoculated medium under anaerobic conditions for a sufficient period of time to permit the growth of a screenable sub-population of microorganisms; and
   (c) identifying in situ those colonies anaerobically expressing amylolytic enzymes by detecting a zone of hydrolyzed starch surrounding each colony.

2. The process according to claim 1, wherein said amylolytic enzymes comprises α-amylase.

3. The process according to claim 1 wherein said detection comprises reaction with a starch indicating reagent.

4. The process of claim 1 wherein said medium comprises a calcium chelating agent.

5. A process for selecting and screening microorganisms for the production of α-amylase which comprises the steps of:
   (a) forming a screening plate comprising a suspension of said microorganisms on a solid medium which promotes the growth of said microorganisms and the synthesis of α-amylase thereby;
   (b) incubating said inoculated medium under anaerobic conditions for a sufficient period of time to permit the growth of a screenable sub-population of microorganisms; and
   (c) identifying in situ those colonies anaerobically expressing α-amylase by detecting a zone of hydrolyzed starch surrounding each colony.

6. The process according to claim 5 wherein said detection comprises reaction with a starch indicating reagent.

7. The process according to claim 5 wherein said medium contains a calcium chelating agent.

* * * * *